United States Patent
Wildermann et al.

(10) Patent No.: US 9,458,096 B2
(45) Date of Patent: *Oct. 4, 2016

(54) PROCESS FOR THE MANUFACTURE OF METHYL LIMONITRILE

(71) Applicant: DSM IP ASSETS B.V., Heerlen (NL)

(72) Inventors: Angela Wildermann, Basel (CH); Werner Bonrath, Basel (CH); Raphael Beumer, Basel (CH); Silke Dorn, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/377,095

(22) PCT Filed: Feb. 11, 2013

(86) PCT No.: PCT/EP2013/052689
§ 371 (c)(1),
(2) Date: Aug. 6, 2014

(87) PCT Pub. No.: WO2013/120808
PCT Pub. Date: Aug. 22, 2013

(65) Prior Publication Data
US 2014/0378695 A1   Dec. 25, 2014

(30) Foreign Application Priority Data

Feb. 15, 2012 (CH) ..................... 00202/12
Feb. 15, 2012 (EP) ..................... 12155595

(51) Int. Cl.
| | |
|---|---|
| *C07C 253/30* | (2006.01) |
| *C07C 255/07* | (2006.01) |
| *C11D 3/50* | (2006.01) |
| *C07C 253/10* | (2006.01) |
| *C07C 253/34* | (2006.01) |

(52) U.S. Cl.
CPC ........... *C07C 253/10* (2013.01); *C07C 253/30* (2013.01); *C07C 253/34* (2013.01)

(58) Field of Classification Search
CPC .. C07C 253/30; C07C 255/07; C11B 9/0023
See application file for complete search history.

(56) References Cited

U.S. PATENT DOCUMENTS

| | | | |
|---|---|---|---|
| 5,011,671 A | * | 4/1991 | Le Loarer ................ B01J 23/10 423/263 |
| 5,663,410 A | | 9/1997 | Beller et al. |
| 2010/0204083 A1 | | 8/2010 | Weis et al. |

FOREIGN PATENT DOCUMENTS

| | | |
|---|---|---|
| CN | 101765584 | 6/2010 |
| EP | 0 152 756 | 8/1985 |
| JP | 45-14532 | 5/1970 |
| JP | 55-73618 | 6/1980 |
| JP | 60-243048 | 12/1985 |
| JP | 08-225507 | 3/1999 |
| JP | 2010-534630 | 11/2010 |
| WO | 2009/013199 | 1/2009 |
| WO | WO 2009/013199 | 1/2009 |

OTHER PUBLICATIONS

International Search Report for PCT/EP2013/052689 mailed Mar. 13, 2013.
Perry's Chemical Engineers' Handbook $6^{th}$ Ed., pp. 1151-1155 (1999).

* cited by examiner

*Primary Examiner* — Nyeemah A Grazier
(74) *Attorney, Agent, or Firm* — Nixon & Vanderhye P.C.

(57) ABSTRACT

The present invention is directed to a process for the manufacture of methyl limonitrile comprising a mixture of 3,7-dimethyl-2,6-nonadiene nitrile, 3,7-dimethyl-3,6-nonadiene nitrile and 7-methyl-3-methylene-6-nonene nitrile comprising the following steps: a) reacting 6-methyl-5-octen-2-one with cyano acetic acid and removing carbon dioxide and water, wherein the reaction and the removal of carbon dioxide and water are performed in the presence of a base and a co-base 1 in an organic solvent, and wherein the organic solvent is a solvent which forms a heteroazeotrop with water; b) removing the solvent and the base of the reaction mixture obtained after having performed step a) or step c) by distillation to obtain a reaction mixture, whereby this step may optionally be performed in the presence of a co-base 2; c) isomerizing the reaction mixture obtained after having performed step a) or step b) to obtain an isomerized reaction mixture in the presence of a co-base 2; whereby step b) can be performed before or after step c).

23 Claims, 6 Drawing Sheets

PROCESS FOR THE MANUFACTURE OF METHYL LIMONITRILE

This application is the U.S. national phase of International Application No. PCT/EP2013/052689 filed 11 Feb. 2013 which designated the U.S. and claims priority to EP 12155595.7 filed 15 Feb. 2012, and CH 00202/12 filed 15 Feb. 2012, the entire contents of each of which are hereby incorporated by reference.

SUMMARY AND BACKGROUND INFORMATION

The present invention is directed to a process for the manufacture of methyl limonitrile. Methyl limonitrile is a mixture of 3,7-dimethyl-2,6-nonadiene nitrile (compound A), 7-methyl-3-methylene-6-nonene nitrile (compound B) and 3,7-dimethyl-3,6-nonadiene nitrile (compound C).

The process according to the invention comprises the step of reacting 6-methyl-5-octen-2-one (6-ethyl-5-hepten-2-one; EH) with cyano acetic acid and removing water and carbon dioxide, wherein the reaction and the removal of water and carbon dioxide are performed in the presence of a base and a co-base and in an organic solvent as shown in FIG. 1.

There is an increasing demand of substituting geranylnitrile by another fragrance, which does not have the toxicological disadvantages of geranylnitrile.

It is already known that methyl limonitrile, a mixture of 3,7-dimethyl-2,6-nonadiene nitrile (compound A), 7-methyl-3-methylene-6-nonene nitrile (compound B) and 3,7-dimethyl-3,6-nonadiene nitrile (compound C), wherein the amount of 7-methyl-3-methylene-6-nonene nitrile and 3,7-dimethyl-3,6-nonadiene nitrile in the mixture is in the range of from 10 to 30 weight-%, based on the total weight of the mixture, does have similar olfactive properties as geranylnitrile.

This especially applies to methyl limonitrile, wherein the ratio of compound A (3,7-dimethyl-2,6-nonadiene nitrile) in methyl limonitrile is in the range of 60 to 90 norm-% (preferably 70 to 85 norm-%, more preferably 76 to 83 norm-%, most preferably around 80 norm-%),
the ratio of compound B (7-methyl-3-methylene-6-nonene nitrile) is in the range of 0 to 10 norm-% (preferably 0 to 5 norm-%, more preferably 0 to 2 norm-%, most preferably around 0 norm-%), and
the ratio of compound C (3,7-dimethyl-3,6-nonadiene nitrile) in methyl limonitrile is in the range of from 10 to 30 norm-% (preferably 15 to 25 norm-%, more preferably 17 to 22 norm-%, most preferably around 20 norm-%), all based on the amount of compounds A, B and C together, where the ratios of A, B and C given in norm-% sum up to a total of 100 norm-%,
and the total amount of methyl limonitrile in the mixture, i.e. the purity, is 95-100 area-% (preferably 97-100 area-%, more preferably 98-100 area-%) as determined by gas chromatography (GC), whereby the conditions for measurement are chosen in a way that all 10 stereoisomers (see FIG. 2) show distinct peaks in the gas chromatogram.

To further illustrate the meaning of "norm-%" an example is given:
In case there is a process product with a purity of methyl limonitrile of 95 area-% and with an amount of compound A of 80 norm-% (A: (A+B+C)=80%), an amount of compound B of 0 norm-% and an amount of compound C of 20 norm-%, that in fact means that the amount of compound A in the process product is 76 area-% (0.95×80%), the amount of compound B in the process product is 0 area-% and the amount of compound C in the process product is 19 area-% (0.95×20%), based on the total weight of the process product.

Such a product is already sold by Givaudan under the tradename "lemonile". Lemonile is a mixture of 3,7-dimethyl-2,6-nonadiene nitrile, 7-methyl-3-methylene-6-nonene nitrile and 3,7-dimethyl-3,6-nonadiene nitrile, wherein the ratio 3,7-dimethyl-2,6-nonadiene nitrile:7-methyl-3-methylene-6-nonene nitrile:3,7-dimethyl-3,6-nonadiene nitrile=80:0:20 with a purity of >98 area-%.

Furthermore there is also a mixture of 3,7-dimethyl-2,6-nonadiene nitrile (compound A), 7-methyl-3-methylene-6-nonene nitrile (compound B) and 3,7-dimethyl-3,6-nonadiene nitrile (compound C) disclosed by BASF in WO 2009/013199 (see WO 2009/013199: page 12, line 33-39), wherein the total amount of B and C is in the range of 0.01 to 10 weight-%, based on the amount of A (in the following called "mixture according to WO 2009/013199"). In case, however, cyano acetic acid and EH were used as starting materials the reaction time was very long (23 hours, see WO 2009/013199: example 1—page 17, line 14-20: (1+7+12+3) hours; example 2—page 18, line 14-20: (1+7+12+3) hours) thus making the process not very attractive. Further disadvantages of this process are the low yields.

At present no process is known to manufacture such a product in an efficient and economic way at industrial scale.

DETAILED DESCRIPTION

Thus, this need is fulfilled by the present invention, which is directed to a process for the manufacture of a mixture comprising 3,7-dimethyl-2,6-nonadiene nitrile, 3,7-dimethyl-3,6-nonadiene nitrile and 7-methyl-3-methylene-6-nonene nitrile comprising the following steps:

a) reacting 6-methyl-5-octen-2-one with cyano acetic acid and removing carbon dioxide and water, wherein the reaction and the removal of carbon dioxide and water are performed in the presence of a base and a co-base 1 in an organic solvent, and wherein the organic solvent is a solvent which forms a heteroazeotrop with water;

b) removing the solvent and the base of the reaction mixture obtained after having performed step a) or step c) by distillation to obtain a reaction mixture, whereby this step may optionally be performed in the presence of co-base 2;

c) isomerizing the reaction mixture obtained after having performed step a) or step b) in presence of co-base 2 to obtain an isomerized reaction mixture; whereby step b) can be performed before or after step c).

With this process lemonile as well as the mixture according to WO 2009/013199 can be produced with high selectivity and yield on an industrial scale making this process economically very attractive.

Starting Materials

Cyano acetic acid (CNA) and 6-methyl-5-octen-2-one (6-ethyl-5-hepten-2-one; EH) are used as starting materials. Usually the molar ratio of CNA to EH is in the range of (0.5 to 1.5 mol):1 mol, preferably in the range of (0.7 to 1.3 mol):1 mol, more preferably in the range of (0.75 to 1.1 mol):1 mol, most preferably in the range of (0.9 to 1.1 mol):1 mol.

Base

Suitable bases are pyridine, 2-methylpyridine, 3-methylpyridine, 2-ethyl pyridine, 3-ethyl-pyridine, 2,3-lutidine (2,3-dimethylpyridine), 2,4-lutidine (2,4-dimethylpyridine), 2,5-lutidine (2,5-dimethylpyridine), 2,6-lutidine (2,6-dimethylpyridine), 2,3,4-collidine (2,3,4-trimethylpyridine), 2,3,5-collidine (2,3,5-trimethylpyridine), 2,3,6-collidine (2,3,6-trimethylpyridine), 2,4,6-collidine (2,4,6-trimethylpyridine), and piperidine, as well as any mixture thereof.

Preferably a single base is used. Of the bases named pyridine, 2-methylpyridine, 3-methylpyridine and piperidine are preferred. More preferred examples are pyridine, 2-methylpyridine and piperidine. The most preferred base is pyridine.

Preferably the amount of the base is in the range of 0.5 to 1.5 mol per mol of EH, more preferably the amount of the base is in the range of 0.7 to 1.3 mol per mol of EH.

Co-Bases 1 and 2

Suitable co-bases 1 are selected from the group consisting of 1,4-diamino butane, 1,5-diaminopentane, piperidine, morpholine, ethylendiamine, diethylentriamine, ammonium acetate and aqueous ammonia solution as well as any mixture thereof.

Preferably a single co-base 1 is used.

Preferred co-bases 1 are ammonium acetate, aqueous ammonia solution, 1,5-diaminopentane, 1,4-diaminobutane and piperidine; more preferred co-bases 1 are ammonium acetate, aqueous ammonia solution, 1,5-diaminopentane and piperidine; even more preferred co-bases 1 are ammonium acetate, aqueous ammonia solution and 1,5-diaminopentane.

Preferably the aqueous ammonia solution has a concentration of around 25 weight-% which is commercially available. It is also possible to use aqueous ammonia solutions with other concentrations such as 10 to 35 weight-% or alcoholic ammonia solutions with ethanol, but the use of an aqueous ammonia solution with a concentration in the range of 25 to 28 weight-% is preferred.

Suitable co-bases 2 are 1,4-diaminobutane (DAB), 1,5-diaminopentane, piperidine and any mixture thereof.

Preferably a single co-base 2 is used.

Preferred co-bases 2 are 1,4-diaminobutane and 1,5-diaminopentan. Most preferably 1,4-diamino butane ("DAB") is used as co-base 2. It is an intermediate produced by DSM as well as by other suppliers.

With all co-bases 1 except of DAB, 1,5-diaminopentane and piperidine it is not possible to get the desired ratio of the stereoisomers of methyl limonitrile (see table 2). Therefore, a co-base 2 has to be added. This addition can be carried out during step b) which has the advantage that the isomerization time for step c) gets shorter (so that the overall process time is shorter) or at the beginning of step c).

If piperidine is used as base, as co-base 1 and as co-base 2 according to a special embodiment of the present invention it has to be made sure that after removal of the solvent in step b) enough piperidine is still present in sufficient amounts and, if not, because it was also partially or completely removed together with the solvent, that it is again added for the isomerization in step c). Preferred solvent in this case is also toluene.

Preferably the amount of the co-base 1 in step a) is in the range of 0.005 to 0.15 mol per mol of EH, more preferably the amount of the co-base is in the range of 0.01 to 0.1 mol per mol of EH, most preferably the amount of the co-base is in the range of 0.01 to 0.05 mol per mol of EH.

Preferably the amount of the co-base 2 in step c) is in the range of 0.005 to 0.15 mol per mol of EH, more preferably the amount of the co-base is in the range of 0.01 to 0.1 mol per mol of EH, most preferably the amount of the co-base is in the range of 0.01 to 0.05 mol per mol of EH.

The co-base may be used as such, i.e. in substance, or also as aqueous solution. This is especially advantageous for 1,4-diaminobutane which has a melting point of 27-28° C. at atmospheric pressure, i.e. it is solid at room temperature, since an aqueous solution of DAB facilitates its dosing. The concentration of such aqueous solution is not critical.

In preferred embodiments of the present invention co-base 1 is selected from the group consisting of ammonium acetate, aqueous ammonia solution, 1,5-diaminpentane and piperidine and co-base 2 is selected from the group consisting of DAB, 1,5-diaminopentane and piperidine.

Solvent

Forming a heteroazeotrop with water means that solvent and water form an azeotrop whereby solvent and water are not or only partially miscible with each other.

Preferred examples of such solvents are toluene, benzene, ortho-xylene, meta-xylene, para-xylene, hexane and heptane and any mixture thereof. More preferred only one solvent of this group is used and not a mixture of two or more solvents. Most preferred toluene is used as solvent.

The amount of solvent is preferably in the range of 0.5 to 2 kg per kg of EH, more preferably the amount of solvent is in the range of 0.8 to 1.5 kg per kg of EH, even more preferably the amount of solvent is in the range of 0.9 to 1.2 kg per kg of EH, most preferably the amount of solvent is in the range of 0.95 to 1.15 kg per kg of EH. These preferred amounts especially also apply if toluene is the solvent.

Reaction Conditions

The manufacture of methyl limonitrile can be divided in several steps which are described in more detail below.

These steps are:

a) reaction of CNA and EH in presence of a base and a co-base 1 in an organic solvent;
b) removal of the organic solvent and the base by distillation optionally in presence of a co-base 2;
c) isomerization of the reaction mixture obtained in step b) to the desired isomer ratio in the presence of a co-base 2;
d) extraction with diluted acids;
e) removal of high boiling impurities ("high boilers");
f) removal of low boiling compounds ("low boilers), recycling of non-reacted 6-ethyl-5-hepten-2-one (EH).

Depending on which of these steps are performed different qualities of the product are obtained which will be described in more detail in the chapter "product".

In the most preferred embodiment of the present invention all preferred conditions for each step a) to f) are realized; pyridine is used as base with the preferred amounts as given above, 1,4-diamino butane is used as co-base 2 with the preferred amounts as given above, toluene is used as solvent with the preferred amounts as given above, and CNA and EH are also used with the preferred amounts as given above.

All steps a) to f) are preferably carried out at inert conditions.

All steps a) to f) can also be carried out either batch-wise or continuously.

A further advantage of the present invention is that steps a) to c) can be carried out as a one-pot-process.

Step a) Reaction

The reaction is carried out at a pressure in the range of from 0.3 to 1.5 bar (absolute pressure), preferably at a pressure in the range of from 0.5 to 1.2 bar (absolute pressure), more preferably at a pressure in the range of from 0.7 to 1.0 bar (absolute pressure). The temperature at which the reaction of EH and CNA and the removal of $H_2O$ and $CO_2$ is performed is defined by the temperature at which the reaction mixture is under reflux.

Step b) Removal of the Solvent and the Base by Distillation

This step is carried out at a final temperature in the range of from 100 to 180° C., preferably at a final temperature in the range of from 120 to 170° C., more preferably at a final temperature in the range of from 130 to 160° C. In case toluene is the solvent and pyridine is the base this step is carried out most preferably at a final temperature in the range of from 140 to 150° C. The distilled off solvent mixture (solvent and base; especially toluene and pyridine) can be used for further reaction batches within the methyl limonitrile production, i.e. it can be recycled back into step a).

The pressure at which this step is performed is preferably in the range of from 0.02 to 1 bar (absolute pressure), preferably in the range of from 0.05 to 1 bar (absolute pressure), more preferably in the range of from 0.1 to 1 bar (absolute pressure).

In case toluene is the solvent and pyridine is the base, the temperature increases up to a temperature in the range of 140 to 150° C. during removal of the solvent mixture. Having reached this temperature the pressure is decreased maintaining this temperature during further removal of the solvent mixture.

It is recommended to almost completely remove the solvent and the base, as well as to recycle them back in step a), optionally after separating low boiling by-products before recycling or purging a part of the solvent mixture.

Optionally a part or the whole amount of co-base 2 can already be added during this process step b) having the advantage that the overall process time is shorter, because the desired isomer ratio of the 10 stereoisomers is reached sooner. Thus, it is preferred to already add here at least a part of the co-base 2.

Step c) Isomerization of the Reaction Mixture Obtained in Step b) to the Desired Isomer Ratio This step is carried out at a temperature in the range of from 100 to 180° C., preferably at a temperature in the range of from 120 to 170° C., more preferably at a temperature in the range of from 130 to 160° C. The pressure at which the isomerization is performed is not relevant and for practical reasons chosen within a range of from 0.1 to 2 bar (absolute pressure). Most convenient this step is performed at atmospheric pressure.

In case the co-base 1 is neither 1,4-diaminobutane nor 1,5-diaminopentane nor piperidine nor any mixture thereof, a co-base 2 has to be added, if not already added in step b). This co-base 2 selected from the group consisting of DAB, 1,5-diaminopentane, piperidine and any mixture thereof is the catalyst for the isomerization reaction.

In principle it is also possible to perform step c) before step b), i.e. that the reaction mixture obtained in step a) is first isomerized (at elevated pressure) and then the solvent and the base are removed, but this version is not recommended since the isomerization is then slower than when step c) is performed after step b), and the isomer ratio may further change during step b) if this step is performed after step c). Furthermore, in case the steps are performed in the order a), c) and b), the amount of the co-base 2 in step c) should be increased to an amount in the range of 0.02 to 0.15 mol per mol of EH to get the preferred desired isomer ratio.

The preferred desired isomer ratio in the context of the present invention is a ratio of 3,7-dimethyl-2,6-nonadiene nitrile (A) to 7-methyl-3-methylene-6-nonene nitrile (B) to 3,7-dimethyl-3,6-nonadiene nitrile (C) in the range of (76 to 83 norm-%) to (0 to 2 norm-%) to (17 to 22 norm-%), especially a ratio of 3,7-dimethyl-2,6-nonadiene nitrile (A) to 7-methyl-3-methylene-6-nonene nitrile (B) to 3,7-dimethyl-3,6-nonadiene nitrile (C) of around 80 norm-% to around 0 norm-% to around 20 norm-%, where the ratios of A, B and C given in norm-% sum up to a total of 100 norm-%.

Step d) Extraction with Diluted Acids

For the extraction of methyl limonitrile from the raw product obtained in step c), in case step c) is performed after step b) (preferred), or from the raw product obtained in step b), in case step b) is performed after step c), preferably an aqueous solution of a strong acid is used as extraction medium.

Examples of such extraction media are aqueous solutions of sulfuric acid, hydrochloric acid and acetic acid, whereby aqueous solutions of sulfuric acid are preferred. More preferred the extraction media have the following concentrations:

Diluted aqueous sulfuric acid: 1-10 weight-%, more preferred 4-8 weight-%;

diluted aqueous hydrochloric acid: 1-10 weight-%, more preferred 4-8 weight-%;

diluted aqueous acetic acid: 5-20 weight-%, more preferred 8-15 weight-%, whereby diluted aqueous sulfuric acid with the concentrations as given above is most preferred.

When the extraction medium is added to the raw product obtained in step c)/b) two phases are formed: an organic phase and an aqueous phase.

The treatment of the crude product obtained in step c)/b) with the extraction medium is preferably carried out at a temperature in the range of from 20 to 90° C., more preferably at a temperature in the range of from 40 to 70° C., most preferably at a temperature in the range of from 50 to 70° C.

The organic phase containing methyl limonitrile is separated from the aqueous phase and washed with deionised water. The washing with deionised water can be carried out several times. It has to be kept in mind that the organic phase contains small amounts of water. This water does not disturb the carrying out of the following step e), but has to be removed after step e) before step f) is performed.

The aqueous phases, i.e. the aqueous phase as obtained when the organic phase is separated off and the combined de-ionised wash waters, can also be back-extracted with the solvent, especially with toluene, whereby a further organic phase is obtained which contains small amounts of water. The back-extraction increases the yield of methyl limonitrile but has the disadvantage in having to remove the solvent again before step e). The removal of the solvent, especially of toluene, may be achieved by rectification or distillation. During the removal of the solvent, especially of the toluene, small amounts of water are also removed.

Step e) Removal of High Boiling Impurities ("High Boilers")

From the organic phase obtained in step d) the coloured components and other high boiling components are removed to gain a clear colorless to light yellow product (so-called "distillate"). This step is also beneficial for the isomer ratio stability. Suitable conditions for this step: distillation at reduced pressure, preferably at a pressure in the range of 0 to 100 mbar (absolute pressure), more preferably at a pressure in the range of 10 to 50 mbar (absolute pressure), most preferably at a pressure in the range of 15 to 30 mbar (absolute pressure).

This step can be carried out in any suitable device known to the person skilled in the art such as e.g. in an evaporator (operated batch-wise or continuously), especially in a thin film evaporator or a fall film evaporator, or in a vessel.

Step f) Removal of Low Boiling Compounds ("Low Boilers), Recycling of Non-Reacted 6-ethyl-5-hepten-2-one (EH)

In case the distillate produced by high boiler removal (product of step e)) is biphasic, which is the case when no back-extraction is carried out in step d) the aqueous phase should be separated before processing further.

The distillate produced by high boiler removal (product of step e)) or (if needed) the organic phase after aqueous phase removal is preferably processed further to a low boiler removal step: the low boiling compounds which contain mainly unconverted EH are separated by distillation or rectification under reduced pressure.

The hereby produced distillate is preferably completely (preferred) or partially taken back to the reaction (step a)) with cyano acetic acid in presence of a solvent (preferred toluene), a base (pyridine) and co-base (DAB) to partially substitute "fresh" EH. Even if all of the fresh EH is substituted by the distillate of the low-boiler removal step, the reaction runs well. Therefore the removal and recycling of unconverted recovered EH is beneficial to increase the overall yield. To avoid accumulation of by-products it might be advantageous to purge a part of this recycle stream from time to time.

The bottom product is the final, well smelling product with a content of >98 area-% of methyl limonitrile.

Product

Methyl limonitrile consists of 10 stereoisomers (compounds A, B and C), wherein 3,7-dimethyl-2,6-nonadiene nitrile (compound A) is in fact a mixture of four stereoisomers as shown in FIG. 2: 3,7-dimethyl-2E,6E-nonadiene nitrile, 3,7-dimethyl-2E,6Z-nonadiene nitrile, 3,7-dimethyl-2Z,6E-nonadiene nitrile and 3,7-dimethyl-2Z,6Z-nonadiene nitrile.

The term "7-methyl-3-methylene-6-nonene nitrile" (compound B) encompasses two stereoisomers, i.e. 7-methyl-3-methylene-6E-nonene nitrile and 7-methyl-3-methylene-6Z-nonene nitrile (see FIG. 2).

3,7-dimethyl-3,6-nonadiene nitrile (compound C) is also a mixture of four stereoisomers (see FIG. 2): 3,7-dimethyl-3E,6E-nonadiene nitrile, 3,7-dimethyl-3E,6Z-nonadiene nitrile, 3,7-dimethyl-3Z,6E-nonadiene nitrile and 3,7-dimethyl-3Z,6Z-nonadiene nitrile.

The product obtained with the process of the present invention is methyl limonitrile,
◇ preferably wherein the ratio of 3,7-dimethyl-2,6-nonadiene nitrile is in the range of 60 to 90 norm-%, the ratio of 7-methyl-3-methylene-6-nonene nitrile is in the range of 0 to 10 norm-%, and the ratio of 3,7-dimethyl-3,6-nonadiene nitrile is in the range of from 10 to 30 norm-%, all based on the amount of compounds A, B and C together, where the ratios of A, B and C given in norm-% sum up to a total of 100 norm-%;
◇ more preferably wherein the ratio of 3,7-dimethyl-2,6-nonadiene nitrile is in the range of 70 to 85 norm-%, the ratio of 7-methyl-3-methylene-6-nonene nitrile is in the range of 0 to 5 norm-%, and the ratio of 3,7-dimethyl-3,6-nonadiene nitrile is in the range of from 15 to 25 norm-%, all based on the amount of compounds A, B and C together, where the ratios of A, B and C given in norm-% sum up to a total of 100 norm-%;
◇ even more preferably wherein the ratio of 3,7-dimethyl-2,6-nonadiene nitrile is in the range of 76 to 83 norm-%, the ratio of 7-methyl-3-methylene-6-nonene nitrile is in the range of 0 to 2 norm-%, and the ratio of 3,7-dimethyl-3,6-nonadiene nitrile is in the range of from 17 to 22 norm-%, all based on the amount of compounds A, B and C together, where the ratios of A, B and C given in norm-% sum up to a total of 100 norm-%;
◇ most preferably wherein the ratio of 3,7-dimethyl-2,6-nonadiene nitrile is around 80 norm-%, the ratio of 7-methyl-3-methylene-6-nonene nitrile is around 0 norm-%, and the ratio of 3,7-dimethyl-3,6-nonadiene nitrile is around 20 norm-%, all based on the amount of compounds A, B and C together, where the ratios of A, B and C given in norm-% sum up to a total of 100 norm-%.

A further preferred mixture is the so-called "mixture according to WO 2009/013199" as defined above.

Depending on which of these steps are performed different qualities of the product are obtained:
◇ If only steps a) to c) or steps a), c) and b) are performed methyl limonitrile of crude quality is obtained. "Crude quality" in the context of the present invention means methyl limonitrile before further purification, but with the desired ratio of the stereoisomers A, B and C as given above in norm-%.
◇ If all steps a) to f) are carried out (see description of the most preferred embodiment of the invention below) methyl limonitrile of olfactive quality is obtained. "Olfactive quality" in the context of the present invention means a pure, colourless, good-smelling product which is suitable for use as flavor and fragrance and has a purity >98 area-%.

Fields of use of methyl limonitrile of olfactive quality are aromatization of consumer articles or everyday commodities. Non-limiting examples of such consumer articles and everyday commodities are cleaning compositions, e.g. scouring compositions, cleaners; care compositions for the treatment of surfaces, e.g. of furniture, floors, kitchen appliances, glass panes and windows, and also windscreens; detergents, softeners; laundry treatment compositions; textile treatment compositions, e.g. ironing aids; and also bleaches and bleach liquors, toilet blocks, limescale removers, air fresheners (air care); fragrance compositions, e.g. for fine perfumery; cosmetic compositions, but also fertilizers, building materials, mold removers, disinfectants, and products for car care.

◇ If step e) (high boiler removal) is not performed the methyl limonitrile is not colourless.
◇ If step f) (low boiler removal) is not performed the methyl limonitrile is stinking.

0.75 mol of CNA, 1.2 mol of pyridine, 0.04 mol of 1,4-diaminobutane and 1 mol of EH, 1.1 kg of toluene per 1 kg of EH, whereby the reaction mixture was held for 4 hours under reflux.

"A" means "compound A", "B" means "compound B" and "C" means "compound C". The X-axis gives the reaction time in hours [h], the Y1-axis (left side) gives the content of compounds A, B and C in [area-%] and the Y2-axis (right side) gives the content of EH in [area-%].

Figure 1:
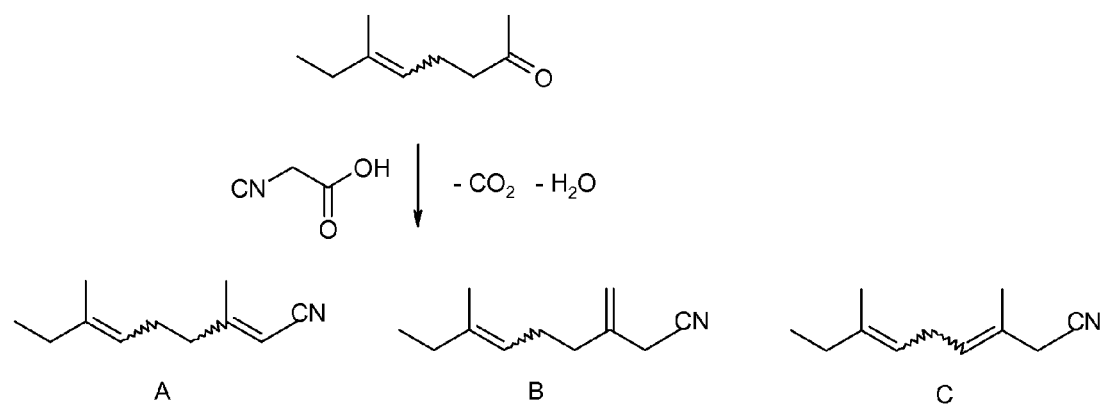
FIG. 1 shows the reaction scheme of the manufacture of methyl limonitrile (step a).
Figure 2:
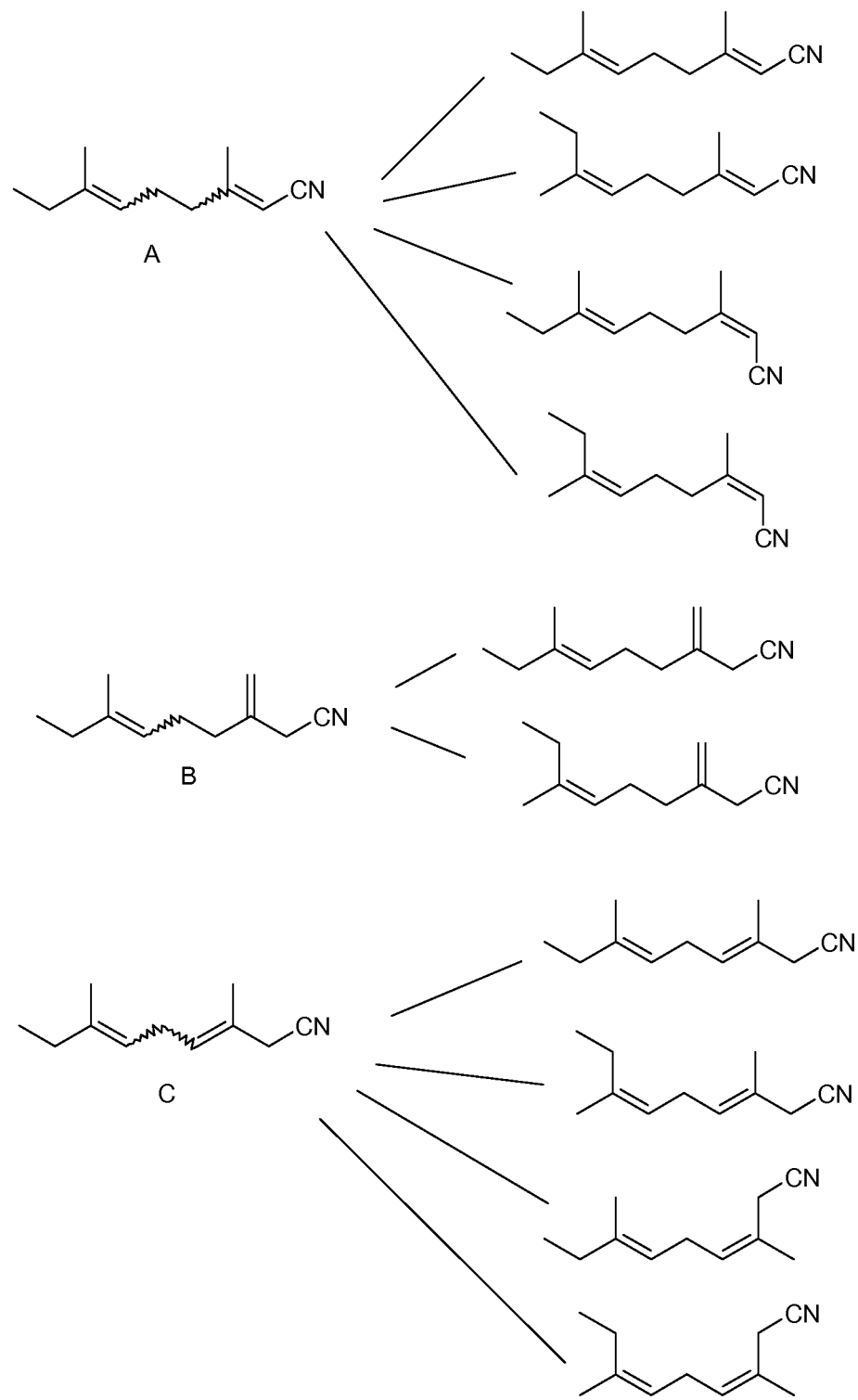
FIG. 2 shows the 10 methyl limonitrile stereoisomers (compounds A, B, C).
Figure 3:
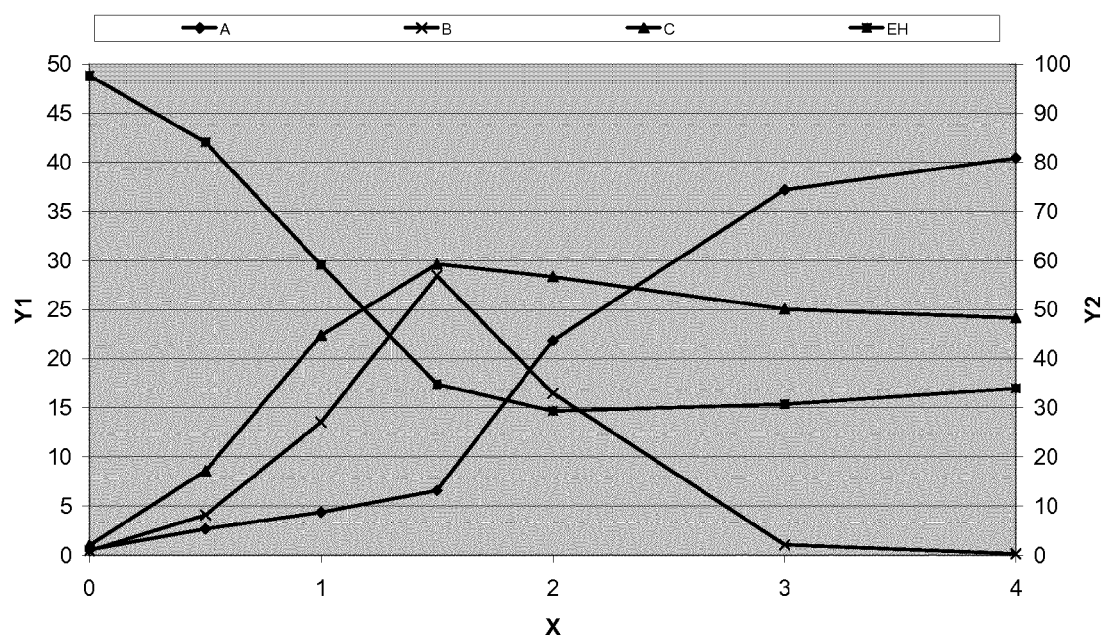
FIG. 3 shows the concentration-time diagram for the following reaction conditions.
Figure 4:
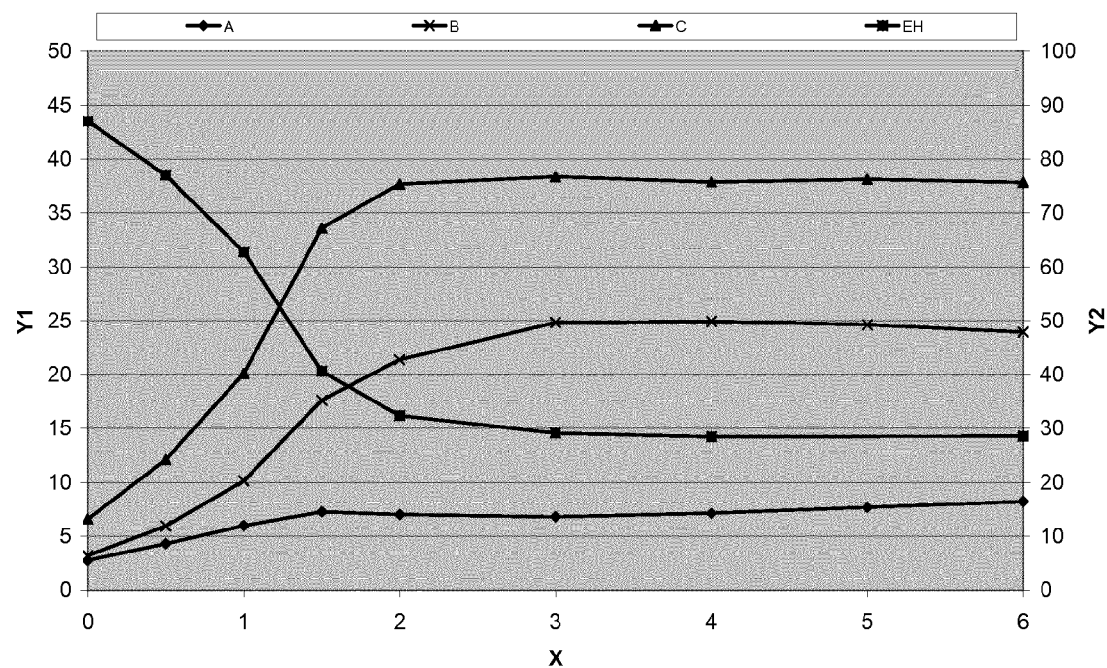

FIG. 4 shows the concentration-time diagram for the following reaction conditions:

0.75 mol of CNA, 1.2 mol of pyridine, 0.04 mol of ammonium acetate and 1 mol of EH, 1.1 kg of toluene per 1 kg of EH, whereby the reaction mixture was held for 6 hours under reflux.

"A" means "compound A", "B" means "compound B" and "C" means "compound C". The X-axis gives the reaction time in hours [h], the Y1-axis (left side) gives the content of compounds A, B and C in [area-%] and the Y2-axis (right side) gives the content of EH in [area-%].

Figure 5:
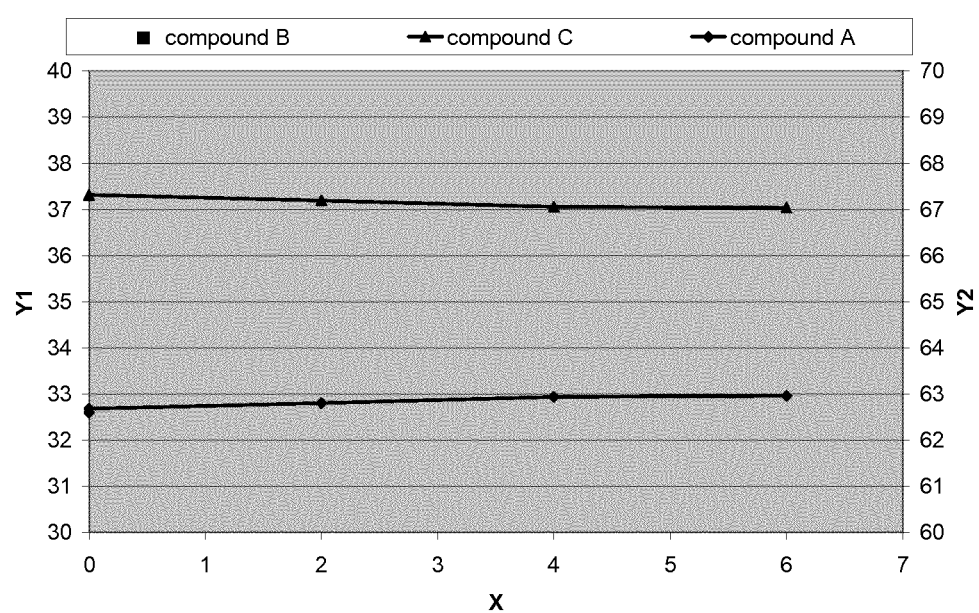

FIG. 5 shows the stability of methyl limonitrile isomers after extraction and high boiler removal at a temperature of 140° C., whereby the X-axis gives the time in hours [h], the Y1-axis (left side) gives the ratio of compounds B and C in [norm-%] and the Y2-axis (right side) gives the ratio of compound A in [norm-%].

Figure 6:
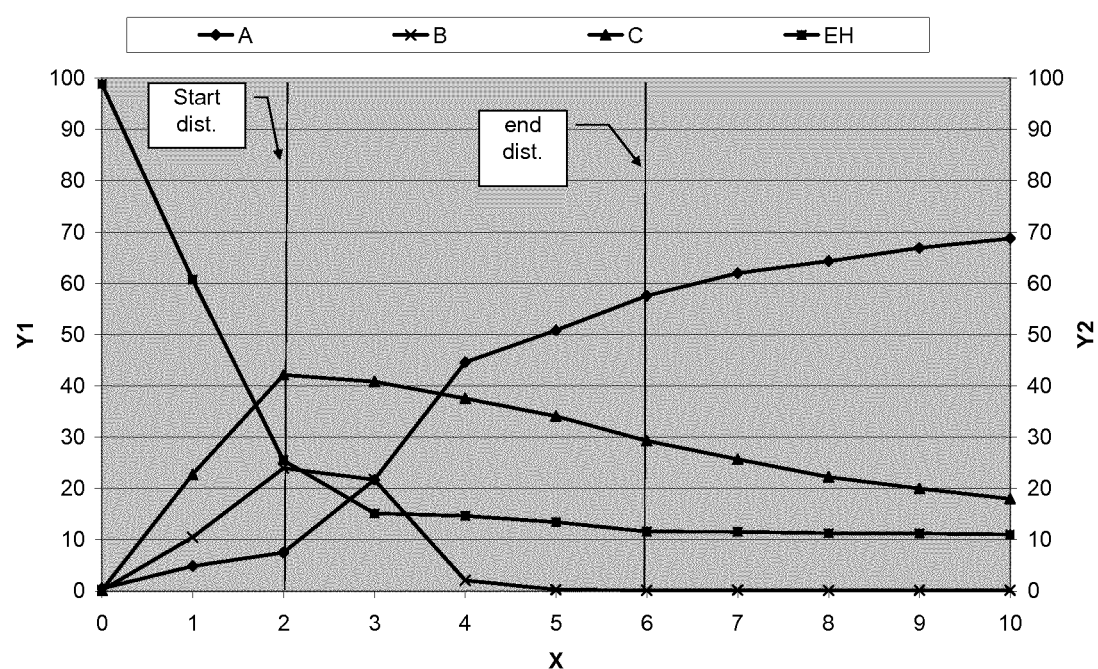

FIG. 6 shows the concentration-time diagram for the whole sequence: reaction (step a)), distillation (step b)), isomerization (step c)) under the following conditions:

Mixture of 1 mol of cyano acetic acid, 1.2 mol of pyridine, 0.01 mol of 1,4-diamino butane and 1 mol of EH as well as 1.1 kg of toluene per 1 kg of EH held under reflux for 2 hours, solvent+base removal (removal of toluene and pyridine) within 4 hours, 4 hours isomerization at 141° C.

"A" means "compound A", "B" means "compound B", "C" means "compound C", "Start dist." means "start of distillation", i.e. starting the removal of pyridine and toluene (step b)), "end dist." means "end of distillation", i.e. end of step b). The X-axis gives the (reaction) time in hours [h], the Y1-axis (left side) gives the content of compounds A, B and C in [area-%] and the Y2-axis (right side) gives the content of EH in [area-%].

MOST PREFERRED EMBODIMENT OF THE PRESENT INVENTION

The most preferred embodiment of the present invention is a process for the manufacture of methyl limonitrile of olfactive quality comprising a mixture of 3,7-dimethyl-2,6-nonadiene nitrile, 3,7-dimethyl-3,6-nonadiene nitrile and 7-methyl-3-methylene-6-nonene nitrile comprising the following steps:

a) reacting 6-methyl-5-octen-2-one with cyano acetic acid and removing carbon dioxide and water, wherein the reaction and the removal of carbon dioxide and water are performed in the presence of pyridine as base and ammonium acetate or aqueous ammonia solution or 1,5-diaminopentane or piperidine or any mixture thereof as co-base 1 (preferably in the presence of ammonium acetate or aqueous ammonia solution or 1,5-diaminopentane as co-base 1) in toluene as organic solvent;

b) removing toluene and pyridine by distillation to obtain a reaction mixture whereby at least a part of co-base 2 (1,4-diaminobutane or 1,5-diaminopentane or piperidine or any mixture thereof; preferably 1,4-diaminobutane or 1,5-diaminopentane, more preferably 1,4-diaminobutane) is added;

c) isomerizing the reaction mixture obtained after having performed step b) to obtain an isomerized reaction mixture in presence of 1,4-diaminobutane or 1,5-diaminopentane or piperidine or any mixture thereof (preferably in presence of 1,4-diaminobutane or 1,5-diaminopentane, more preferably in presence of 1,4-diaminobutane) as co-base 2;

d) extracting the isomerized reaction mixture with diluted acids whereby an organic phase and an aqueous phase are formed, separating the organic phase containing the methyl limonitrile from the aqueous phase, and washing the organic phase one or more times with deionized water;

d-2) optionally back-extracting the aqueous phase obtained in step d) with toluene and afterwards removing the toluene, whereby the thus removed toluene is optionally recycled into step d-2);

e) separating off coloured components and high boiling impurities from the organic phase obtained in step d);

f) separating off low boiling impurities from the distillate obtained in step e) to achieve the olfactive quality, whereby these low boiling impurities are mainly EH;

f2) optionally recycling the EH obtained in step f) back into step a).

Steps a), b), c), d), e) and f) are performed as described above, also with the preferred conditions as given.

It should be kept in mind that in case piperidine is co-base 1 and co-base 2 it is advantageous to add it again in step b) since part of it may be removed together with the toluene and/or pyridine so that the isomerization reaction is faster. This also applies for the case where piperidine is base, co-base 1 and co-base 2.

Step d2)

The back-extraction with toluene increases the overall yield of methyl limonitrile but has the disadvantage in having to remove the toluene again before step e). The removal of the toluene may be achieved by rectification or distillation and can be carried out batch-wise or continuously.

Thus, preferably the back-extraction is not carried out. If it is, however, carried out, the thus removed toluene is advantageously recycled back into step d-2) and used again for further back-extraction.

In case the distillate produced by high boiler removal (product of step e)) is biphasic, the water phase should be separated before processing further. This is the case when no back-extraction is carried out.

Step f2)

Preferably this step is performed, i.e. the thus removed unconverted EH is completely (preferred) or partially recycled back into step a).

The term "methyl limonitrile mixture of olfactive quality" means that the purity of this mixture is >98 area-%.

The invention is now further illustrated in the following non-limiting examples.

EXAMPLES

Example 1

I) Preparation of Methyl Limonitrile

In a 0.5 liter reactor (double jacketed) with condenser, dean stark apparatus and stirrer 153 g (ca. 180 ml) of toluene, 85.5 g (1 mol) of cyano acetic acid, 140 g (1 mol) of ethylheptenone (EH), 99 g of pyridine, and 0.95 g (0.01 mol) of 1,4-diaminobutane are filled into the reactor under $N_2$ and heated up. The mixture is held under reflux for 2 hours including water and carbon dioxide removal. Subsequently the solvent (mainly consisting of toluene and pyridine) is slowly distilled off within 4 hours. Thereby the inner temperature increases to 141° C. and for nearly complete removal of the solvents vacuum is applied (down to 200 mbar absolute pressure) by maintaining an inner temperature of 141° C. Afterwards the reaction mixture is isomerized within four additional hours at 141° C. to achieve the desired isomer ratio. The reaction mixture is weighed (148.8 g) and analysed by GC: 11 weight-% EH, 78.8 weight-% methyl limonitrile (isomer ratio A:B:C=80.2:0.1:19.6—all in norm-%).

Result: EH conversion: 85.6%; yield methyl limonitrile based on EH: 75.3%; selectivity methyl limonitrile based on EH: 87.9%.

II) Extraction of the Reaction Mixture 145.1 g of the reaction mixture obtained in I are washed with 52.1 g of diluted sulfuric acid (8 weight-% $H_2SO_4$ in water) for 30 minutes at 60° C. After phase separation the organic layer is additionally washed with 49.3 g of deionised water at 60° C. The combined water layers are back washed with 41.8 g of toluene at 60° C. This back extraction of the aqueous layers with toluene can be skipped with only minor losses of yield. Skipping of the toluene back washing results in skipping of the toluene distillation step as well.

Result: Extraction yield methyl limonitrile: 99.7%.

III) Toluene and High Boiler Removal 49.8 g of the combined organic layers (extraction, back extraction) are distilled in a rotary evaporator at a bath temperature of 100° C. and 30 mbar for ½ hour to remove the toluene (5.23 g). Afterwards the bath temperature is increased to 180° C. 34.83 g of distillate with the following composition are obtained: 4 weight-% of toluene, 14 weight-% of EH, 79 weight-% of methyl limonitrile (A:B:C=72.3:0.2:27.5). The high boiling impurities remain as residue.

Result: yield methyl limonitrile in distillate: 92% (i.e. 92% of the methyl limonitrile used for the distillation). In another example a yield of 96.5% was achieved.

IV) Recycling of Non-Reacted 6-ethyl-5-hepten-2-one (EH)

The distillate produced by high boiler removal (see III) is processed further to a low boiler removal step: the low boiling compounds, mainly EH and toluene, are separated by distillation or rectification under reduced pressure. The hereby produced distillate is taken back to the reaction with cyano acetic acid in presence of toluene, pyridine and 1,4-diaminobutane (DAB) to partially substitute "fresh" EH. Even if all of the fresh EH is substituted by the distillate of the low-boiler removal step, the reaction runs well. Therefore the removal and recycling of unconverted EH is beneficial to increase the overall yield.

Examples 2 to 7

Variation of the Base

The results of the examples 2 to 7 are summarized in the enclosed table 1.

The conversion is based on the amount of 6-ethyl-5-hepten-2-one (EH).

The yield is the molar amount of methyl limonitrile based on the molar amount of 6-ethyl-5-hepten-2-one.

The selectivity is the molar amount of methyl limonitrile, based on the molar amount of converted 6-ethyl-5-hepten-2-one.

The examples are performed as described under Example 1—I) and II), i.e. without performing steps III) and IV). If the conditions differ from the ones of example 1 the differences are given here or in table 1.

Reaction time (step a)): 6 hours (at reflux) if not indicated otherwise; 0.25 hours distillation (step b)), 0 hour isomerization (step c)).

Molar ratio cyano acetic acid:6-ethyl-5-hepten-2-one=0.75 mol/mol.

It is not possible to get the desired ratio of the stereoisomers of methyl limonitrile with ammonium acetate as cobase, see examples 5 and 6 in table 1, as the compounds C do not isomerize further to the compounds A.

Examples 8 to 19

Variation of the Co-Base

The results of the examples 8 to 19 are summarized in the enclosed table 2.

The conversion is based on the amount of 6-ethyl-5-hepten-2-one.

The yield is the molar amount of methyl limonitrile, based on the molar amount of 6-ethyl-5-hepten-2-one.

The selectivity is the molar amount of methyl limonitrile, based on the molar amount of converted 6-ethyl-5-hepten-2-one.

The examples are performed as described under Example 1—I) and II), i.e. without performing steps III) and IV). If the conditions differ from the ones of example 1 the differences are given here or in table 2.

Reaction time (step a)): 4 hours (at reflux) if not indicated otherwise, 0.25 hours distillation (step b)), 0 hour isomerization (step c)).

Molar ratio cyano acetic acid:6-ethyl-5-hepten-2-one:=0.75 mol/mol.

Examples 20 to 39

Pyridine-1,4-diaminobutane a) Examples 20 to 22

Variation of the Amount of Cobase 1,4-diaminobutane

The results are summarized in table 3 below. The examples are performed as described under Example 1—I) and II), i.e. without performing steps III) and IV). If the conditions differ from the ones of example 1 the differences are given here or in table 3.

Amount of cyano acetic acid=0.75 mol; amount of 6-ethyl-5-hepten-2-one (EH)=1 mol; amount of pyridine=1.25 mol.

Reaction time (step a)): 4 hours (at reflux) if not indicated otherwise; 0.25 hours distillation (step b)), 0 hour isomerization (step c)).

TABLE 3

| Example | Molar ratio 1,4-diaminobutane:EH | Ratio A:B:C [norm-%] | Conversion [%] | Yield [%] | Selectivity [%] |
|---|---|---|---|---|---|
| 20 | 0.012 | 55:3:42 | 64.9 | 56.3 | 87 |
| 21 | 0.022 | 62:0:38 | 65 | 61.5 | 94.6 |
| 16 | 0.043 | 70:0:30 | 63.8 | 58.4 | 91.6 |
| 22 | 0.088 | 74:0:26 | 65.7 | 51.4 | 78.2 | b) Examples 23 to 26

Variation of the Amount of the Base Pyridine

The results are summarized in table 4 below. The examples are performed as described under Example 1—I) and II), i.e. without performing steps III) and IV). If the conditions differ from the ones of example 1 the differences are given here or in table 4.

Amount of cyano acetic acid=0.75 mol; amount of 6-ethyl-5-hepten-2-one (EH)=1 mol; amount of 1,4-diaminobutane=0.04 mol.

Reaction time (step a)): 4 hours (at reflux) if not indicated otherwise; 0.25 hours distillation (step b)), 0 hour isomerization (step c)).

TABLE 4

| Example | Molar ratio pyridine:EH | Ratio A:B:C [norm-%] | Conversion [%] | Yield [%] | Selectivity [%] |
|---|---|---|---|---|---|
| 23 | 1.264 | 66:0:34 | 68.9 | 52.6 | 76.3 |
| 24 | 1.065 | 68:0:32 | 70.5 | 55.0 | 78.0 |
| 25 | 0.798 | 70:0:30 | 68.9 | 63.1 | 91.6 |
| 26 | 0.541 | 69:0:31 | 74.4 | 55.9 | 75.1 | c) Examples 27 to 29

Variation of the Amount of Cyano Acetic Acid

The results are summarized in table 5 below. The examples are performed as described under Example 1—I) and II), i.e. without performing steps III) and IV). If the conditions differ from the ones of example 1 the differences are given here or in table 5.

Amount of cyano acetic acid: x mol, amount of pyridine=1.65·x mol; amount of 6-ethyl-5-hepten-2-one (EH)=1 mol; amount of 1,4-diaminobutane=0.04 mol.

Reaction time (step a)): 4 hours (at reflux) if not indicated otherwise; 0.25 hours distillation (step b)), 0 hour isomerization (step c)).

TABLE 5

| Example | Molar ratio cyano acetic acid:EH | Ratio A:B:C [norm-%] | Conversion [%] | Yield [%] | Selectivity [%] |
|---|---|---|---|---|---|
| 16 | 0.795 | 70:0:30 | 63.8 | 58.4 | 91.6 |
| 27 | 0.902 | 65:0:35 | 69.6 | 65 | 93.3 |
| 28 | 0.998 | 60:0:40 | 75.9 | 68.4 | 90 |
| 29 | 1.066 (1.25 · x mol of pyridine) | 41:0:39 | 81.5 | 67.4 | 82.7 | d) Examples 30 to 32

Variation of the Dosage Time of 6-ethyl-5-hepten-2-one (EH)

The results are summarized in table 6 below. The examples are performed as described under Example 1—I) and II), i.e. without performing steps III) and IV). If the conditions differ from the ones of example 1 the differences are given here or in table 6.

Amount of cyano acetic acid=0.75 mol; amount of 6-ethyl-5-hepten-2-one (EH)=1 mol; amount of pyridine=1.3 mol; amount of 1,4-diaminobutane (DAB)=0.04 mol.

Reaction time (step a)): 4 hours (at reflux) if not indicated otherwise, 0.25 hours distillation (step b)), 0 hour isomerization (step c)).

TABLE 6

| Example | Dosage time in hours | Ratio A:B:C [norm-%] | Conversion [%] | Yield [%] | Selectivity [%] |
|---|---|---|---|---|---|
| 30 | 0 | 63:0:37 | 62.6 | 51.4 | 82.2 |
| 31 | 2 | 61:0:39 | 62.7 | 48.0 | 76.6 |
| 32 | 3 | 62:0:38 | 59.8 | 45.8 | 76.5 | e) Examples 33 to 39

Influence of the Temperature, the Amount and the Concentration of the Co-Base on the Isomerization The results are summarized in the enclosed table 7. The examples are performed as described under Example 1—I. If the conditions differ from the ones of example 1 the differences are given here or in table 7.

Amount of cyano acetic acid=1 mol; amount of 6-ethyl-5-hepten-2-one (EH)=1 mol; amount of pyridine=1.2 mol;

2 hours at reflux, 2 hours for (partial) solvent removal, 4 hours for isomerization.

f) Examples 40 to 42

Recycling of Unconverted EH

The results are summarized in table 8 below. The examples are performed as described under Example 1—I. If the conditions differ from the ones of example 1 the differences are given here or in table 8.

Amount of cyano acetic acid=1 mol; amount of 6-ethyl-5-hepten-2-one=1 mol; amount of pyridine=1.3 mol, amount of 1,4-diamino butane=0.01 mol.

2 hours at reflux (700 mbara), 4 hours for solvent removal, 2 hours for isomerization at 141° C.

TABLE 8

| Example | Purity of 6-ethyl-5-hepten-2-one [weight-%] | Ratio A:B:C [norm-%] | Conversion [%] | Yield [%] | Selectivity [%] |
|---|---|---|---|---|---|
| 40 | 96.7 8 (fresh) | 78:0:22 | 90.4 | 78.7 | 87.0 |
| 41 | 90.1 (distillate) | 80:0:20 | 88.6 | 76.6 | 86.4 |
| 42 | 77.2 (distillate) | 83:0:17 | 90.4 | 79.4 | 87.9 |

As can be seen from table 8 unconverted EH can successfully be used for further reaction batches.

TABLE 1

Variation of the base

| Example | Base | Amount of base [mol/mol EH] | Co-base 1 | Amount of co-base [mol/mol EH] | Ratio A:B:C [norm-%] | Conversion [%] | Yield [%] | Selectivity [%] |
|---|---|---|---|---|---|---|---|---|
| 2 | pyridine | 1.14 | none | 0 | 7:34:59 | 33.6 | 19 | 56.5 |
| 3 | pyridine | 1.14 | ammonium acetate (NH$_4$OAc) | 0.04 | 12:34:54 | 66.8 | 63 | 94.4 |
| 4 | pyridine | 1.23 | NH$_4$OAc | 0.04 | 12:36:52 | 67.3 | 61.4 | 91.2 |
| 4A | 2-methyl pyridine | 1.21 | NH$_4$OAc | 0.04 | 8:42:50 | 59.1 | 58.4 | 99 |
| 5 | Pyridine (24 hours) | 1.23 | NH$_4$OAc | 0.04 | 22:24:54 | 68.2 | 63.4 | 93.0 |
| 6 | Pyridine (48 hours) | 1.24 | NH$_4$OAc | 0.04 | 39:9:52 | 66.4 | 63.1 | 94.9 |
| 7 | piperidine | 1.22 | NH$_4$OAc | 0.04 | 99:0:1 | 39 | 34.6 | 88.7 |

TABLE 2

Variation of the co-base

| Example | Base | Amount of base [mol] | Co-bases | Amount of co-base [mol] | Ratio A:B:C [norm-%] | Conversion [%] | Yield [%] | Selectivity [%] |
|---|---|---|---|---|---|---|---|---|
| 8 | pyridine | 1.31 | aqueous ammonia solution (25 weight-%) (co-base 1) | 0.05 | 8:38:54 | 63.7 | 65.8 | 103 |
| 9 | pyridine | 1.32 | aqueous ammonia solution (25 weight-%) (co-base 1) and after 2 hours 1,4-diaminobutane (co-base 2 added in step b) | 0.15 0.01 | 49:7:44 | 72.0 | 57.1 | 79.33 |
| 10 | pyridine (6 hours) | 1.14 | piperidine (co-base 1) | 0.04 | 58:0:42 | 38.1 | 31.6 | 83.1 |
| 11 | pyridine | 1.14 | morpholine (co-base 1) | 0.04 | 11:39:50 | 46.7 | 43.7 | 93.8 |
| 12 | pyridine | 1.32 | ethylene diamine (co-base 1) | 0.05 | 59:1:40 | 72.2 | 61.7 | 85.6 |
| 13 | pyridine | 1.24 | diethylene triamine (co-base 1) | 0.04 | 67:0:33 | 67.5 | 57.0 | 84.4 |
| 14 | pyridine | 1.27 | 1,4-diaminobutane (co-base 1) | 0.01 | 55:3:42 | 64.7 | 56.3 | 87.0 |
| 15 | pyridine | 1.27 | 1,4-diaminobutane (co-base 1) | 0.04 | 68:0:32 | 70.6 | 51.8 | 73.3 |
| 15A | 2-methyl pyridine | 1.29 | 1,4-diaminobutane (co-base 1) | 0.04 | 63:0:37 | 59.5 | 43.7 | 73.4 |
| 16 | pyridine | 1.31 | 1,4-diaminobutane (co-base 1) | 0.04 | 70:0:30 | 63.8 | 58.4 | 91.6 |
| 17 | pyridine (6 hours) | 1.31 | 1,4-diaminobutane (co-base 1) | 0.04 | 70:0:30 | 68.7 | 52.8 | 76.9 |
| 18 | pyridine | 1.32 | 1,4-diaminobutane (co-base 1) | 0.04 | 68:0:32 | 68.5 | 54.3 | 79.3 |
| 19 | pyridine | 1.32 | NH$_4$OAc (co-base 1) and after 2 hours 1,4-diaminobutane (co-base 2 added in step b) | 0.04 0.01 | 37:16:47 | 69.7 | 58.1 | 83.4 |

TABLE 7

| Example | Amount of co-base DAB [mol/mol EH] | Residual solvent (toluene/pyridine) [weight-%] | Isomerization Temperature [° C.] | Ratio A:B:C [norm-%] | Conversion [%] | Yield [%] | Selectivity [%] |
|---|---|---|---|---|---|---|---|
| 33 | 0.01 | <5 | 143 | 75:0:25 | 86.7 | 77.2 | 89.0 |
| 34 | 0.01 | <5 | 168 | 91:0:9 | 87.1 | 70.6 | 81.1 |
| 35 | 0.02 | <5 | 143 | 91:0:9 | 91.2 | 71.8 | 78.7 |
| 36 | 0.01 | 40 | 132 | 61:0:39 | 84.3 | 75.3 | 89.3 |
| 37 | 0.01 | 29 | 143 | 60:0:40 | 82.8 | 75.1 | 90.7 |
| 38 | 0.01 | 20 | 153 | 76:0:24 | 85.8 | 73.5 | 85.7 |
| 39 | 0.01 | <5 | 168 | 91:0:9 | 87.1 | 70.6 | 81.1 |

The invention claimed is:

1. A process for the manufacture of methyl limonitrile comprising a mixture of 3,7-dimethyl-2,6-nonadiene nitrile, 3,7-dimethyl-3,6-nonadiene nitrile and 7-methyl-3-methylene-6-nonene nitrile, wherein the process comprises the following steps:
    a) reacting 6-methyl-5-octen-2-one with cyano acetic acid and removing carbon dioxide and water, wherein the reaction of 6-methyl-5-octen-2-one with cyano acetic acid and the removal of carbon dioxide and water are performed in the presence of a base and a co-base 1 in an organic solvent which forms a heteroazeotrop with water;
    b) removing the organic solvent and the base of a mixture obtained after having performed step a) or step c) by distillation, optionally in the presence of a co-base 2; and
    c) isomerizing the mixture obtained after having performed step a) or step b) in the presence of a co-base 2 to obtain an isomerized reaction mixture; wherein step b) can be performed before or after step c), and wherein the co-base 2 is selected from the group consisting of 1,4-diaminobutane, 1,5-diaminopentane, piperidine and mixtures thereof.

2. The process according to claim 1, wherein the organic solvent is at least one selected from the group consisting of toluene, benzene, ortho-xylene, meta-xylene, para-xylene, hexane, and heptane.

3. The process according to claim 1, wherein the organic solvent is toluene.

4. The process according to claim 1, wherein the steps are performed in the order a), b) and c) such that step b) is performed before step c).

5. The process according to claim 1, which further comprises recycling the solvent and the base removed from the mixture back into step a).

6. The process according to claim 1, further comprising additional steps comprising:
    d1) extracting the isomerized reaction mixture with diluted acids to form an organic phase and an aqueous phase,
    d2) separating the organic phase containing the methyl limonitrile from the aqueous phase, and
    d3) washing the organic phase one or more times with deionized water.

7. The process according to claim 6, comprising the additional step of back-extracting the aqueous phase with the solvent and removing the solvent.

8. The process according to claim 6, further comprising an additional step of e) separating off coloured components and high boiling impurities from the organic phase.

9. The process according to claim 6, further comprising an additional step of f) separating off the low boiling impurities.

10. The process according to claim 9, wherein the low boiling impurities contain unconverted low boiling 6-methyl-5-octen-2-one, and wherein the process comprises an additional step of at least partially recycling the low boiling 6-methyl-5-octen-2-one back to the reaction of step a).

11. The process according to claim 1, which comprises the following steps:
    a) reacting 6-methyl-5-octen-2-one with cyano acetic acid and removing carbon dioxide and water, wherein the reaction of 6-methyl-5-octen-2-one with cyano acetic acid and the removal of carbon dioxide and water are performed in the presence of pyridine as a base and a co-base 1 in toluene as an organic solvent, wherein the co-base 1 is at least one selected from the group consisting of ammonium acetate, an aqueous ammonia solution, 1,5-diaminopentane, and piperidine;
    b) removing toluene and pyridine by distillation to obtain a reaction mixture and adding to the reaction mixture at least a part of a co-base 2 selected from the group consisting of 1,4-diaminobutane, 1,5-diamino-pentane, piperidine and mixtures thereof;
    c) isomerizing the reaction mixture obtained after having performed step b) in presence of at least one co-base 2 selected from the group consisting of 1,4-diaminobutane, 1,5-diaminopentane, and piperidine to obtain an isomerized reaction mixture;
    d) extracting the isomerized reaction mixture with a diluted acid to form an organic phase and an aqueous phase, separating the organic phase containing the methyl limonitrile from the aqueous phase, and washing the organic phase one or more times with deionized water;
    d-2) optionally back-extracting the aqueous phase obtained in step d) with toluene and thereafter removing the toluene, whereby the thus removed toluene is optionally recycled into step d-2);
    e) separating off coloured components and high boiling impurities from the organic phase obtained in step d);
    f) separating off low boiling impurities from the distillate obtained in step e), whereby these low boiling impurities are mainly unconverted 6-methyl-5-octen-2-one; and
    f2) optionally recycling the 6-methyl-5-octen-2-one obtained in step f) back into step a).

12. The process according to claim 1, wherein the molar ratio of cyano acetic acid to 6-methyl-5-octen-2-one is in a range of 0.5 to 1.5 mol cyano acetic acid per 1 mol 6-methyl-5-octen-2-one.

13. The process according to claim 11, wherein the amount of pyridine is in a range of 0.5 to 1.5 mol pyridine per mol of 6-methyl-5-octen-2-one.

14. The process according to claim 11, wherein the amount of 1,4-diaminobutane is in a range of 0.005 to 0.15 mol 1,4-diaminobutane per mol of 6-methyl-5-octen-2-one.

15. The process according to claim 1, wherein the amount of solvent is in a range of 0.5 to 2 kg solvent per kg of 6-methyl-5-octen-2-one.

16. The process according to claim 1, wherein the 3,7-dimethyl-2,6-nonadiene nitrile, the 7-methyl-3-methylene-6-nonene nitrile and the 3,7-dimethyl-3,6-nonadiene nitrile sum to a total of 100 norm-%, and wherein the 3,7-dimethyl-2,6-nonadiene nitrile is present in a range of 60 to 90 norm-%, the 7-methyl-3-methylene-6-nonene nitrile is present in a range of 0 to 10 norm-%, and the 3,7-dimethyl-3,6-nonadiene nitrile is present in a range of from 10 to 30 norm-%.

17. The process according to claim 16, wherein the 3,7-dimethyl-2,6-nonadiene nitrile is present in the range of 70 to 85 norm-%, the 7-methyl-3-methylene-6-nonene nitrile is present in the range of 0 to 5 norm-%, and the 3,7-dimethyl-3,6-nonadiene nitrile is present in the range of from 15 to 25 norm-%.

18. The process according to claim 16, wherein the 3,7-dimethyl-2,6-nonadiene nitrile is present in a range of 76 to 83 norm-%, the 7-methyl-3-methylene-6-nonene nitrile is present in a range of 0 to 2 norm-%, and the 3,7-dimethyl-3,6-nonadiene nitrile is present in a range of from 17 to 22 norm-%.

19. The process according to claim 16, wherein the amount of 3,7-dimethyl-2,6-nonadiene nitrile is around 80 norm-%, the amount of 7-methyl-3-methylene-6-nonene nitrile is around 0 norm-%, and the amount of 3,7-dimethyl-3,6-nonadiene nitrile is around 20 norm-%.

20. The process according to claim 1, wherein a total amount of 3,7-dimethyl-3,6-nonadiene nitrile and 7-methyl-3-methylene-6-nonene nitrile is in a range of 0.01 to 10 weight-%, based on the amount of 3,7-dimethyl-2,6-nonadiene nitrile.

21. The process according to claim 1, wherein the base is at least one selected from the group consisting of pyridine, 2-methyl pyridine, 3-methyl pyridine, 2-ethyl pyridine, 3-ethyl-pyridine, 2,3-lutidine, 2,4-lutidine, 2,5-lutidine, 2,6-lutidine, 2,3,4-collidine, 2,3,5-collidine, 2,3,6-collidine, 2,4,6-collidine, and piperidine.

22. The process according to claim 1, wherein the co-base 1 is at least one selected from the group consisting of 1,4-diamino butane, 1,5-diaminopentane, piperidine, morpholine, ethylendiamine, diethylentriamine, ammonium acetate and aqueous ammonia solution.

23. The process according to claim 1, wherein the co-base 1 is at least on selected from the group consisting of ammonium acetate, aqueous ammonia solution, 1,5-diaminopentane, 1,4-diaminobutane and piperidine.

* * * * *